United States Patent [19]
Bowen

[11] Patent Number: 5,603,921
[45] Date of Patent: Feb. 18, 1997

[54] MEDICATED DENTAL FLOSS AND METHOD OF PREPARATION

[75] Inventor: Mark A. Bowen, Stowe, Mass.

[73] Assignee: Whalen Biomedical Incorporated, Somerville, Mass.

[21] Appl. No.: 403,182

[22] Filed: Mar. 13, 1995

[51] Int. Cl.⁶ .................................................. A61K 7/16
[52] U.S. Cl. ............................................................ 424/49
[58] Field of Search ................................................ 424/49

[56] References Cited

U.S. PATENT DOCUMENTS 5,423,337  6/1995  Ahlert ...................................... 132/321

OTHER PUBLICATIONS

Xu Chem Abst 119: 103129 1993.

*Primary Examiner*—Paul J. Killos

[57] ABSTRACT

A medicated dental floss and a method of preparation is presented for controlling the bacterial activity associated with gingivitis. The floss incorporates an antimicrobial agent which, as a result of the flossing action, is deposited to the interdental area of the teeth. The slow dissolution of the antimicrobial agent ensures that effective levels of medication are attained for sustained periods, thereby reducing bacterial activity.

4 Claims, 6 Drawing Sheets

LUBRICANT PATH

MEDICATED DENTAL FLOSS AND METHOD OF PREPARATION

The U.S. government has a paid up license in this invention and the right, in limited circumstances to require the patent owner to license others on reasonable terms as provided by the terms of SBIR Phase I Grant 1243DE 10566-01 awarded by the National Institute of Dental Research.

BACKGROUND—DESCRIPTION OF PRIOR ART

This invention relates to an improved dental floss of the antibacterial type. The purpose of the proposed research is to develop a novel means of drug delivery for controlling gingivitis utilizing a dental floss with medication laden lubricant. Bacterial activity is indicated in the majority of gingivitis occurrences. Research efforts have been directed at investigating antimicrobial agents such as stannous fluoride, taurolin, and chlorhexidine for their effectiveness in reducing the levels of the most commonly encountered bacterial strains in the oral environment with encouraging results. The bulk of these efforts have resulted in the development of the antimicrobial agent in the form of a mouth rinse.

Plaque is the leading cause of tooth decay and periodontal disease, affecting approximately 90% of the adult population. Plaque is a sticky colorless layer of harmful bacteria that is constantly forming on teeth and gums. To reduce the incidence of periodontal disease, plaque should be removed at least once a day. Generally, the typical means for removing plaque deposits involves brushing, using a toothbrush, preferably combined with use of dental floss and/or toothpicks. Recently, the use of rotary electric toothbrushes has gained favor as a more effective means for removing plaque and, therefore, for preventing and reducing the incidence of periodontal disease.

Periodontitis is a painful and destructive dental disease which accounts for the majority of tooth loss in adult populations. Though the disease is widespread, certain groups have developed a higher rate of affliction. Among these are the elderly, patients undergoing cancer therapy, and other patient populations experiencing immunosuppression, such as HIV infected individuals. Other susceptible individuals include patients receiving orthodonture and fixed prosthodontics.

The most common aspect of periodontitis is oral tissue destruction and eventual loss of teeth. However, this disease may be successfully prevented in the early stage of development known as gingivitis. Gingivitis is recognized by inflammation, and often bleeding, of the gingiva and is associated with an increase in dental plaque and calculus deposits. Conditions leading to the initiation and progression of gingivitis, as well as the histopathological features associated with gingival inflammation have been thoroughly documented in the canine model.

With the formation of the supragingival plaque adhering to the enamel surface of the teeth, plaque derived substances enter the gingival tissues by diffusion. The gingiva reacts in response to these substances in a variety of ways. To begin with, the natural stream of emigrating neutrophils becomes intensified. Next, the connective tissue covering the gingival margin becomes acutely inflamed. Permeability of the vessels increases and their morphology changes. This is accompanied by an exudation of neutrophils and monocytes, as well as serum components. In addition, there is the appearance of gingival fluid, degradation of the collagen framework at the site of the reaction, and development of a cellular infiltrate at this site.

Though the identification of the specific factors within the plaque which are directly responsible for the onset of inflammation is still in debate, there is no doubt that bacterial plaque is essential for the production of gingival inflammation in both the human and canine models. Increases in the magnitude and maturity of plaque deposits have been shown to be linked to significant alterations in the oral microfloral environment which favor the growth of certain bacterial types.

Studies of gingivitis have documented that normal gingiva did not harbor these bacteria and that the change in the microflora occurred before gingivitis was clinically diagnosed, indicating that these microorganisms play a role in the initiation of periodontal inflammation. Thus, the most effective means of preventing or reversing gingivitis would involve a combination of bacterial eradication and plaque removal.

The most common recommendation for plaque removal is mechanical, through scaling, planing, and polishing, followed up by regular tooth brushing and flossing. Studies have shown that plaque accumulation is highest in the interdental regions, causing gingival conditions to become most serious in these areas. Thus, it is important to focus on plaque removal and bacterial reduction in these areas.

While these methods are effective in removing plaque formed on teeth, periodontal disease is still prevalent in the adult population and, consequently, improved means for the treatment of periodontal disease are still indicated. In particular, attempts have been made to develop means for delivering various medicaments to the areas subject to periodontal disease and other diseases, in order to combat these diseases in place.

A common antibacterial agent used widely in both clinical and domestic applications is chlorhexidine. Chlorhexidine is a cationic biguanide microbicide with a broad spectrum of activity against many forms of bacteria and fungi. It has been shown to be effective in reducing the activity of many common strains of oral flora and has been a popular agent in many studies of gingivitis reversal. Specifically, chlorhexidine acts to directly disrupt the permeability of the bacterial cell membrane leading to lethal destruction of the cell. Most research in this area has been conducted using chlorhexidine gluconate oral rinses. These studies have revealed many positive aspects of this antimicrobial agent but also many negative aspects of the rinse application.

Chlorhexidine has been shown to have many beneficial properties in dental applications, in addition to its general antibacterial activity. Chlorhexidine gluconate adsorbs to hydroxyapatite, tooth surfaces, and salivary mucins and is subsequently released when the concentration in the environment is low. This affinity may in part be due to the cationic binding of chlorhexidine to the acidic side chains of proteins found in saliva and oral tissues. These mucins continuously cover the teeth and the oral mucosa, and their incorporation in the plaque matrix has been suggested.

Thus, reservoirs of chlorhexidine may form which would be slowly released, preventing bacterial colonization and the development of dental plaque. However, when chlorhexidine is applied in the form of an oral rinse, the contact time between the agent and the oral cavity is very brief. Even a contact time of one minute showed a 25% reduction in adsorption as compared to a contact time of 5 minutes. In addition, the constant flow of phosphate and chloride ions, and mucins in the mouth will tend to rapidly eliminate free chlorhexidine from the mouth. Generally, oral rinses are the preferred means for delivering medicaments to these diseased areas. However, such oral rinses suffer from the inability to penetrate significantly below the gum line and may not contact the gum line.

In an effort to improve the adsorption and beneficial activity of these types of preparations, systems have been developed, but with significant shortcomings. Specifically, a medicament containing dental brush, U.S. Pat. No. 5,373,599 by Lemon, includes a plurality of parallel fibers having a medicament such as tetracycline, chlorhexidine, or sodium fluoride disposed between or within the individual fibers. The medicament is then released during brushing. However, a device of this nature which utilizes a dental brush as a means for drug delivery, can be extremely painful to patients with advanced disease, there is also the issue of reliable drug delivery to the sight of infection. Once the brush is removed the source of the drug is interrupted making the absorption similar to that of a mouth rinse. Specifically, the drug does not remain at the site of infection for any appreciable amount of time.

Tseng, U.S. Pat. No. 5,340,581 shows a sustained release matrix for dental application which includes either an antimicrobial agent or a colorant that is released from the matrix when the matrix contacts water. The matrix consists of a polyethylene oxide incorporated into the bristles on a tooth brush. Upon contact with water some of the anti-microbial agent diffuses out of the matrix, onto and down the bristles and eventually into the saliva and mouth killing bacteria on contact. The ability of the drug to stay on the tooth or infected surface is compromised however, when the source of the drug is removed, i.e. the tooth brush. Once the mechanical act of brushing is discontinued drug is no longer available.

U.S. Pat. No. 3,830,247 discloses dental floss impregnated with antiseptic in a housing wherein the floss passes through a reservoir of antiseptic. U.S. Pat. No. 3,342,539 discloses a dental floss which comprises a length of conventional construction terminating in a porous section which when pre-soaked prior to use, in an antiseptic solution, then delivered into interdental spaces as the floss is used normally to physically remove food particles from between the teeth. U.S. Pat. No. 3,838,702 shows a dental floss having an improved cleaning and polishing action obtained by coating the floss with a coating agent comprised of a resilient wax, polymer or elastomer, having embedded therein a finely divided, particulate, polishing agent. In addition, the incorporation of various adjuvant materials into the coating agent such as coloring matter, flavoring, medicinals or therapeutic agents is suggested.

Thus, a more feasible and effective method of application is with the use of a chlorhexidine impregnated dental floss. Rosenberger, U.S. Pat. No. 5,280,796 relates to a dental floss coated with a microcrystalline wax containing a prophylactic, antimicrobial analgesic and/or antiseptic material. However, microcrystalline wax, as described by Rosenberger, is hydrophobic and therefore resistant to transfer to the moist surface of the teeth, which minimizes its effectiveness as a vehicle for medication delivery.

The transfer of antibacterial agent is limited to that material which resides on the surface of the wax. Such a limited quantity is unlikely to provide an effective concentration within the mouth once the floss is removed. In addition, this concentration will be rapidly diluted by the influx of saliva. The antimicrobial effect of the drug is shortened, as the medication is quickly washed away. The quantity of drug available at the surface of the wax may be enhanced by increasing the percentage of drug within the wax, however, high percentages of drug will reduce the effectiveness of the wax as a lubricant or binder, and will adversely effect the handling characteristics of the floss.

U.S. Pat. No. 3,897,795 makes use of a soap or detergent binder for binding bacterially active matter into the floss material. The application may take place through using squeegees and/or squeegee rollers, by using a volatile ingredient as a solvent for the active agent and/or binder or by pulling the floss through a paste mix of the active agent.

For the purposes of a drug delivery system, it is desirable that the lubricant transfer to the tooth surface and dissolve, leaving the antibacterial agent in place, as indicated by Tseng, this is not the case. In contrast, the present invention mechanically removes plaque deposits, and delivers a dosage of chlorhexidine compound to the surfaces with the greatest risk of disease: the interdental region, supragingival region and subgingival regions. This is accomplished by incorporating the antimicrobial agent into the dental floss lubricant, a soluble vehicle such as Polyethylene Glycol. For the purpose of a drug delivery system it is desirable that the lubricant transfer to the tooth surface and dissolve, leaving the antibacterial agent in place.

The action of flossing will deposit small amounts of the soluble vehicle directly to the areas in need of treatment: the interdental spaces that are difficult to reach by other means. These areas, particularly the subgingival regions, are relatively shielded from the constant flux of saliva, which results in the retardation of the dissolution of the vehicle. This slow dissolution of the antimicrobial agent will ensure that effective levels of medication are maintained at the divider sites for greater periods than attainable with mouth rinses. The precise placement of the medication will result in greater effectiveness with the use of significantly less medication than through oral rinsing. Staining, which is common with frequent oral rinsing, should also be reduced or limited to areas that are largely concealed, reducing aesthetic impact.

The subsequent reduction of bacteria in these areas combats gingival inflammation without affecting the general oral flora. Likewise, the chlorhexidine compound will be shielded from rapid removal due to the constant flow of mouth mucins and elements. Staining will also be confined to the interdental spaces presenting less of an aesthetic burden to the patient. Medicated antibacterial floss such as this could prove especially useful in many specific situations.

As will be seen hereinafter, none of the previously cited art discloses applicant's novel, unique, and unobvious product which overcomes the prejudice of the prior art against a wax binder of coating for floss where bactericidal material is incorporated in the floss.

SUMMARY OF THE INVENTION

With the above in view, the primary objectives of this invention resides in a process by which a lubricant is applied to a dental floss of sufficiently small diameter to permit insertion between the teeth, coated with a soluble vehicle, such as polyethylene glycol, containing a prophylactic, antimicrobial material.

It is another object of the invention to provide a dental floss comprising a flexible length of floss having at least on the exterior thereof a coating of a broad spectrum microbicide, such as a cationic biguanide microbicide, generally known as chlorhexidine.

It is another objective of this invention to provide a dental floss with a surface coated with a soluble vehicle, such as polyethylene glycol, impregnated with a therapeutic agent, such as an antimicrobial.

It is another objective of the invention to provide a dental floss with a surface coated with a water soluble vehicle, such that the soluble vehicle is impregnated with a therapeutic agent, such as an anti microbial, which, when the action of flossing is employed, deposits small amounts of said vehicle with the therapeutic agent on to the tooth surface.

It is yet another object of the invention to disperse the therapeutic agent to the interdental and gingivival areas of the teeth.

DESCRIPTION OF THE DRAWINGS

The structure, operation, and advantage of this invention will become further apparent upon consideration of the following description taken in conjunction with the accompanying drawings.

DETAILED DESCRIPTION OF THE INVENTION

Figure 1:
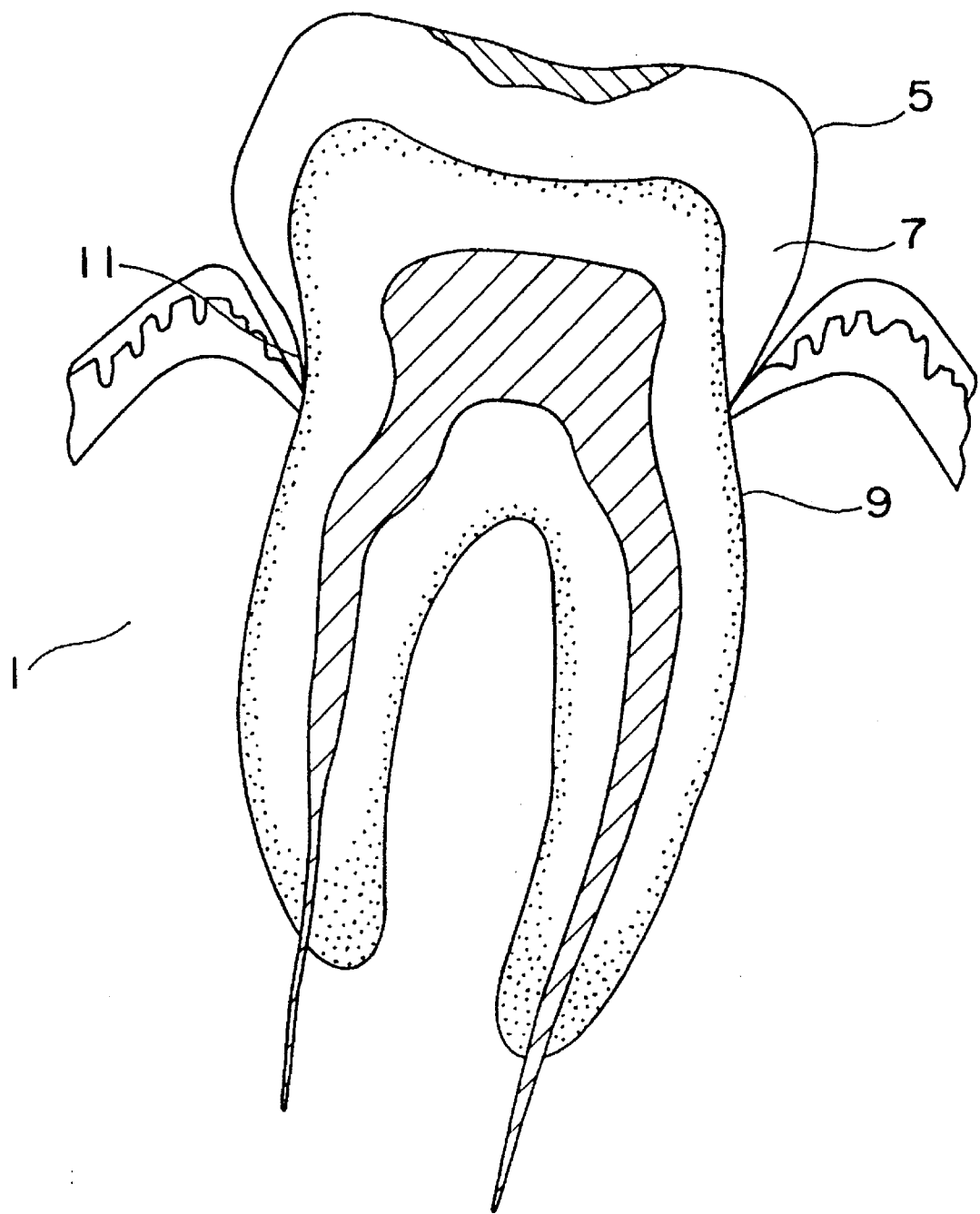
FIG. 1 is a cross sectional view of a healthy tooth.

Referring now to the drawings, FIG. 1 shows a healthy tooth, as generally indicated at 1. It is seen that a healthy tooth has enamel 5 of the tooth 1, and that the tooth cementum 7, is not exposed. The aveolar bone 9 extends nearly to the cementoenamel junction 11 to form a deep socket for the tooth 1.

Figure 2:
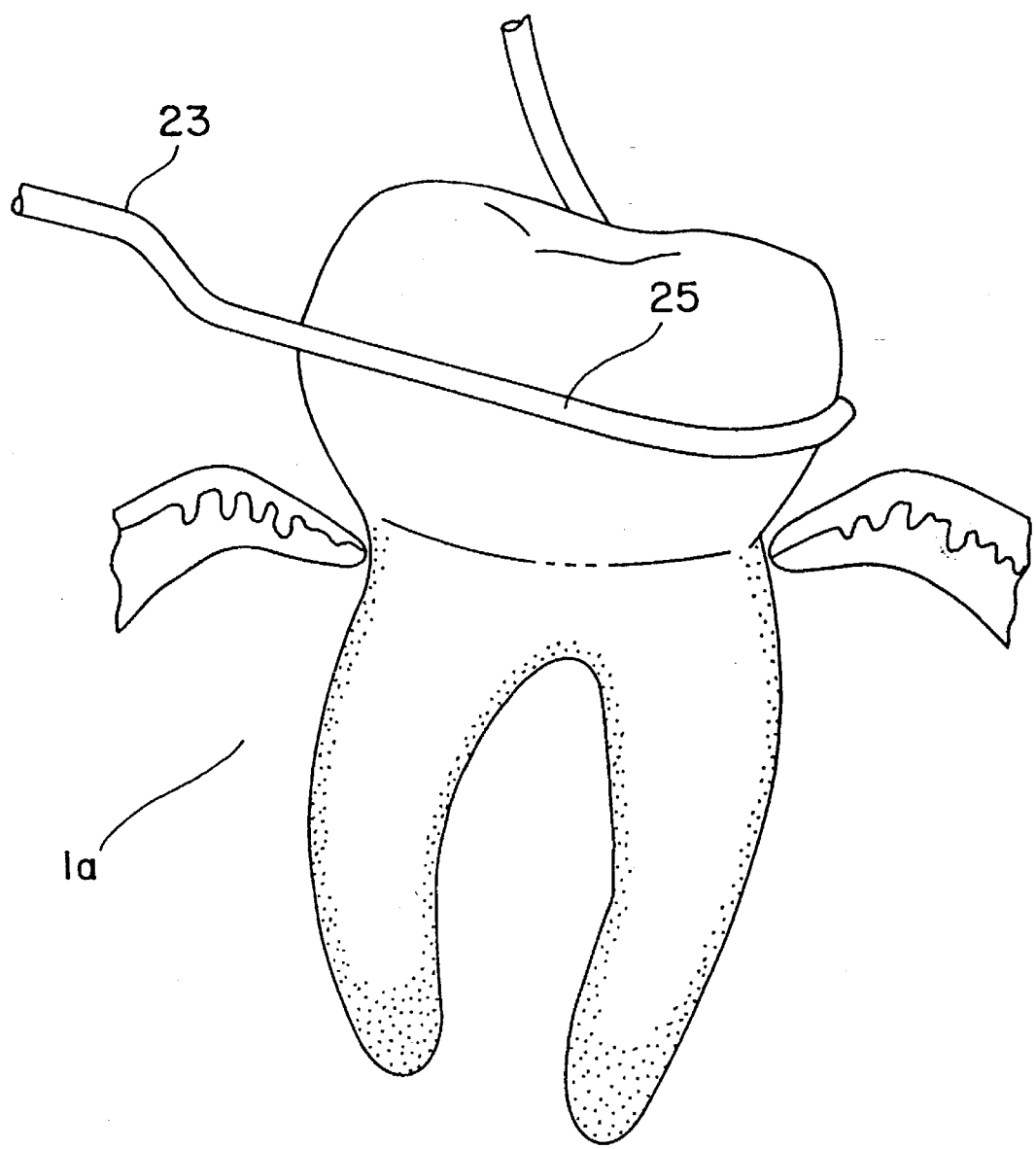
FIG. 2 is a cross sectional representation of the dental floss laden with the soluble vehicle containing anti microbicide.

Referring now to FIG. 2 dental floss 23 is indicated, having a means for holding a supply of medicament 25 for direct application to the infected site as the teeth are flossed in the usual manner.

Figure 3:
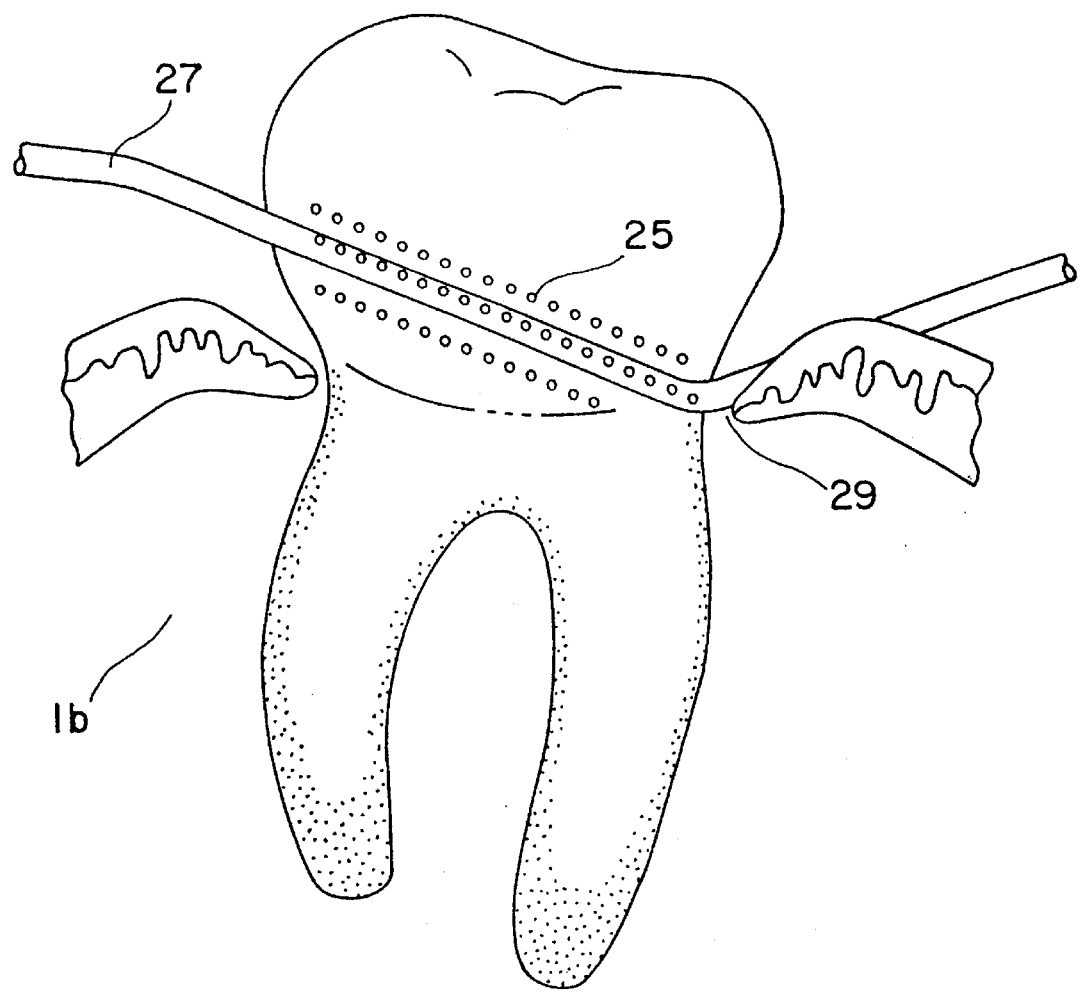
FIG. 3 illustrates the use of the anti microbial containing floss on the surface of a tooth.

Referring now to FIG. 3 best results are obtained when medicament 25a is delivered directly to the infected site. The delivery is simplified by the present invention. Floss 27a is pretreated so as to hold a supply of the preferred medicament, preferably chlorhexidine, sufficient to treat all of the affected teeth. Floss 27a is worked by the patient in the usual manner in the interdental spaces such that the floss 27a is forcibly drawn below gingiva 29a so as to wipe the medicament carried by floss 27a directly on to the infected site. When floss 27a is properly used the medication laden lubricant is deposited directly on, is delivered in close proximity to, or is brought into actual contact with the area affected by the periodontal disease.

The traditional waxed dental floss consists of non-twisted nylon yarn impregnated with a microcrystalline petroleum wax. The wax serves two purposes. First, it provides a level of lubrication which facilitates the passing of the floss between the teeth. Second, it bonds the individual strands together in a form preferred by many patients. Due to its hydrophobic qualities and insolubility in saliva, the petroleum wax does not transfer to the moist surface of the teeth, thus avoiding long term buildup.

For the purpose of a drug delivery system, it is desirable that the lubricant transfer to the tooth surface and dissolve, leaving the antibacterial agent in place. We chose polyethylene glycol (PEG) as the base lubricant. PEG is used in a wide variety of industrial, food, cosmetic, and pharmaceutical applications. Pharmaceutical grades of PEG's are available in a range of molecular weights from 200 to 8000. An increase in molecular weight is accompanied by an increase in hardness and melting temperature and a decrease in water solubility and flexibility. PEG's of differing molecular weight may be blended to arrive at a combination that delivers the optimal properties. It is important to mention that other pharmaceutical constituents, such as polyvinylalcohol, may be employed on a similar manner. In addition, combinations of constituents may be employed to attain desired properties such as specific rates of dissolution, melting points, lubricity, solubility of therapeutic agents, or to improve the handling or packaging of the product. Such embodiments will be obvious to those familiar with the Art and are thus within the spirit of the described invention.

One preparation yielding a practical balance of properties was a blend of two parts PEG 3350 and one part PEG 1000, which became liquid at a temperature of 60° C. with a viscosity of 190 cP. This combination reliably saturated the virgin floss, cooled to a solid state quickly, adhered well to the floss when cool, was possessed of a desirably waxy feel, was sufficiently flexible so as not to flake off the floss when handled, and did not transfer excessively to the hands.

Figure 4:
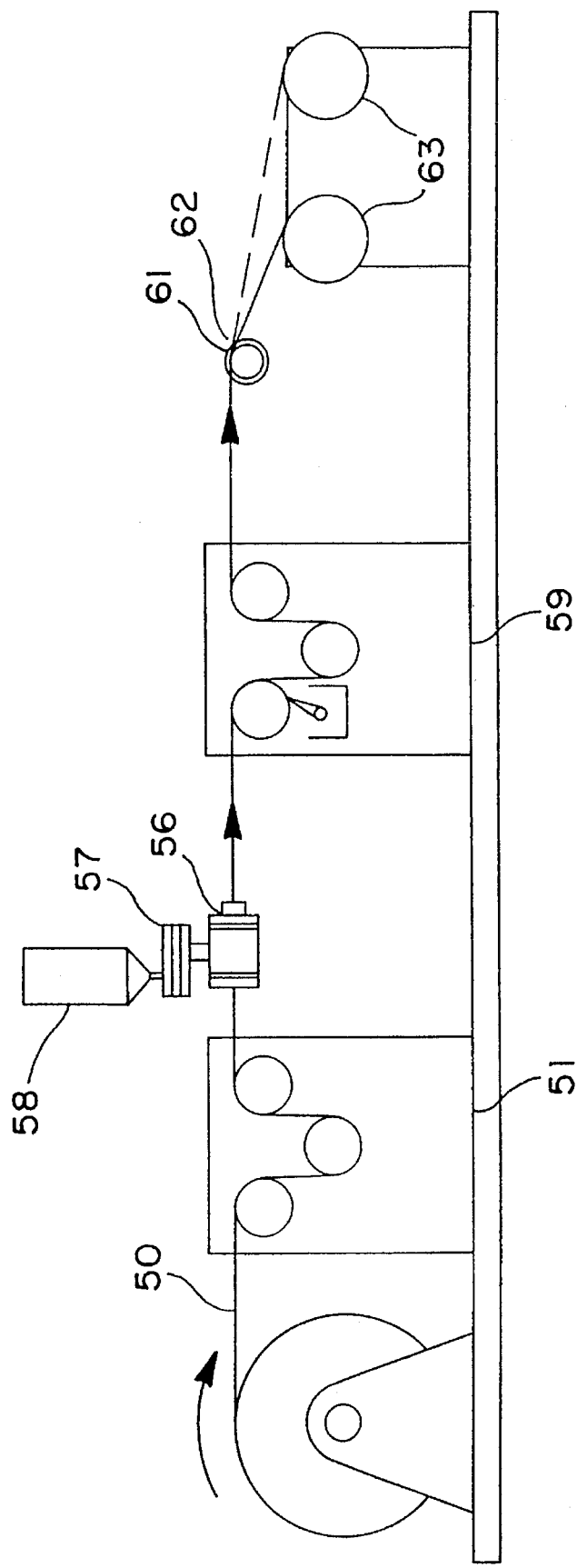
FIG. 4 is a schematic representation of the floss coating process.

Turning to FIG. 4, the coating operation is illustrated, floss 50 is drawn from the supply spool by three roll traction capstan 51, then routed to coating die 53. Three roll traction capstan 51 consists of three 12 cm diameter chrome plated cylindrical rolls; two upper rolls 54 and one lower roll 55. Upper rolls 54 rotate in the same direction, lower roll 55 rotates in the opposite direction. The speed of the rolls is governed by a direct current motor and a servo feedback speed control. The floss 50 to be coated is passed over first upper roll 54, below lower roll 55, and over final upper roll 55. This provides 360° of wrap angle and a large surface area, which enables positive transport of the fiber with a minimum of contact pressure, as well as an effective interface for heat transfer.

The moving floss is then directed through cross head coating die 56, which applies the molten lubricant. The lubricant preparations are provided in solid granular or flake form which is premelted and fed into melt pump 57. Premelter 58, consists of a cylindroconical hopper with a heated grid. The solid lubricant preparation melts as it comes in contact with the grid and is then be directed to melt pump 57.

After passing through die 56, floss 50 will require a period of time to allow the PEG to cool and solidify. The only means of allowing this time on a continuously running line is to provide sufficient travel distance between the die and second traction capstan 59. Capstan roll surfaces 59 provide additional cooling capacity by virtue of the large contact area and heat sinking mass. To avoid the problem of lubricant transferring to the capstan roll, scraping blade 60 bears against its surface to remove any adhering material before it has a chance to build up to nuisance levels.

After cooling, coated floss 50 is directed to a take-up station where it is wound onto spools under controlled tension. As it is being wound, guide pulleys 61 direct floss 50 to traverse the width of spool 62, laying it down in an orderly fashion which avoids tangles and undue bonding between layers. The take-up mechanism is provided by revolving spindles 63, to allow the floss to be transferred to a fresh spool when the other spool becomes filled. Thus the coating process can proceed without interruption.

Spindles 63, are driven by a DC servo controlled motor, and contain control brakes to limit winding tension. In operation, the take-up spindle speed is set to a level slightly higher than that of the traction capstans, the difference in speed being made up by slippage in the tension brake. This method will ensure consistent tension throughout the spool regardless of the increase in package diameter as more layers of floss are wound.

A certain minimum tension is required to maintain control of the moving floss, and this tension setting must be held within reasonable limits. Tension control is important to the coating operation because variations in tension will cause the floss to stretch unevenly, making an accurate control of the lubricant loading per unit length of product impossible. If the floss is stretched excessively while passing through the coater and the rate of lubricant delivery is constant, the actual quantity of lubricant applied to the floss will be more than that desired when it is allowed to revert to its natural length.

Figure 5:
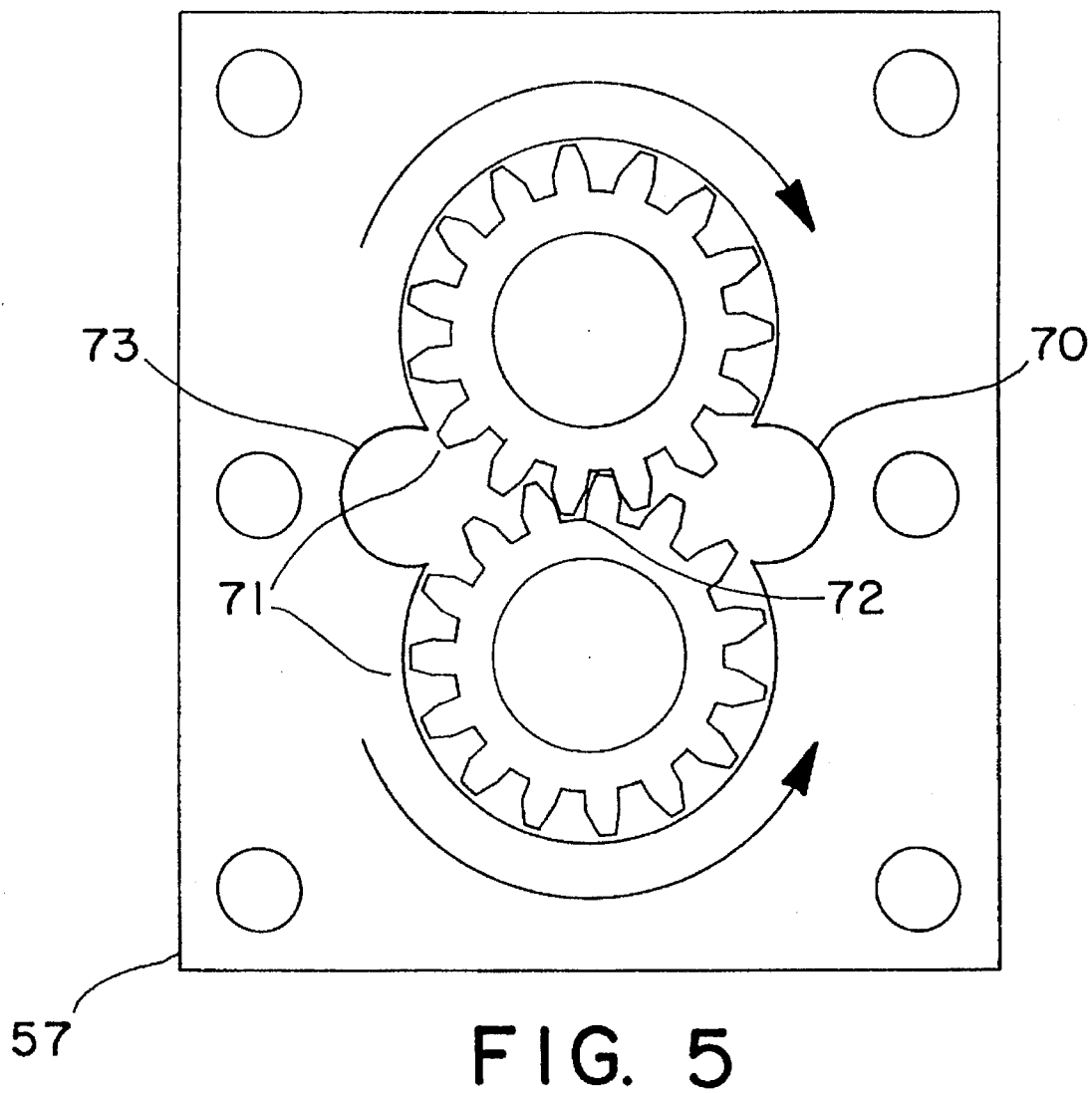
FIG. 5 is a sectional view of the gear pump.

Turning now to FIG. 5, melt pump 57 is a heated, gear type, positive displacement metering pump consisting of two intermeshing gears housed in a closely fitting plate. FIG. 5 is a schematic representation of typical melt pump operation.

FIG. 5 shows melt pump 57 in operation, fluid enters inlet port 70. Gears 71 rotate, forcing fluid to occupy the minute volume between each gear tooth 72. Fluid is then transported to outlet port 73.

Figure 6:
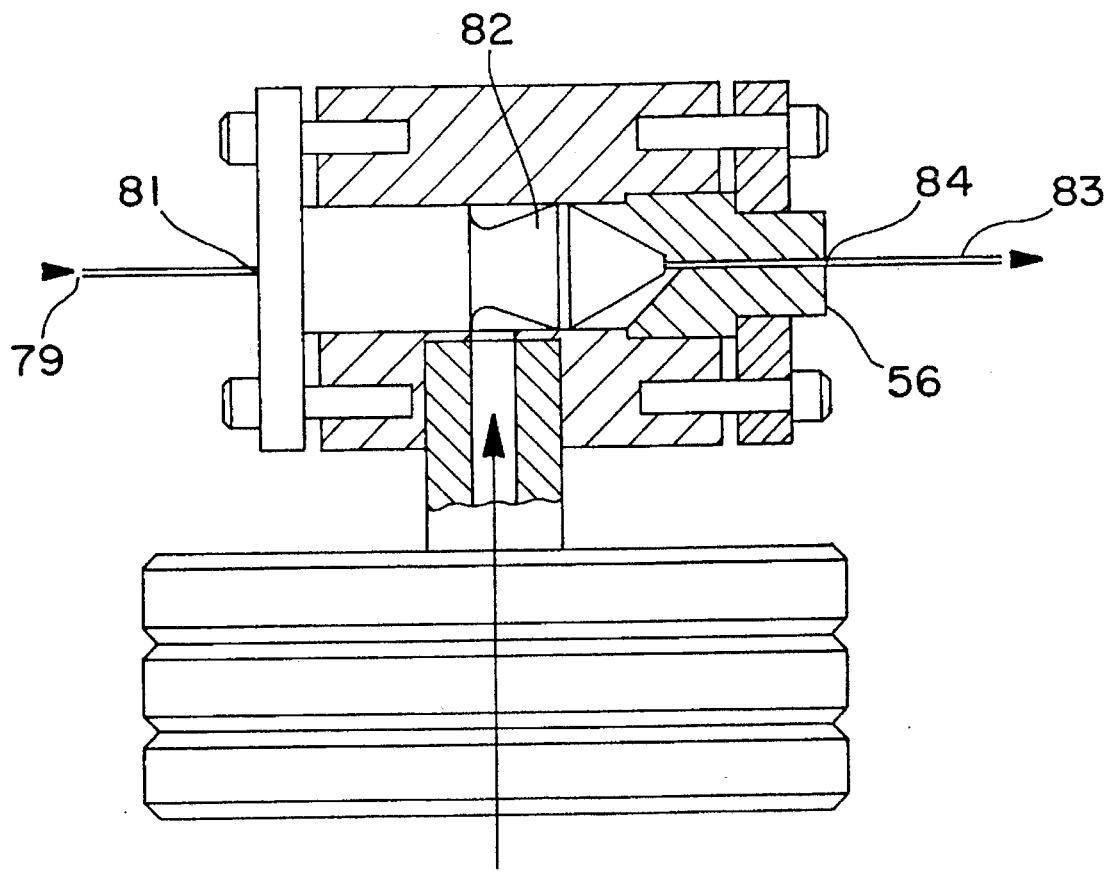
FIG. 6 is a sectional view of the coating die.

Coating die 56 is of a cross head configuration, wherein the melted material is introduced to the die head along a path which is perpendicular to the path of the finished product, more easily seen in FIG. 6. Moving floss 83 enters through fitted hole 79. Melted material is introduced via side port 81, and is directed by flow divider 82, to surround floss 83 in a balanced manner. Floss 83 then exits die 56 by passing through fitted orifice 84.

The dimensions of the orifice are important. It is desirable for the pressure within the die to be significantly above atmospheric to promote thorough saturation of the floss. Thus, the diameter of the opening must be the minimum which will allow ready passage of the floss, while the length of the die must be sufficient to allow the pressure to drop from the coating pressure to near ambient at the exit of the die.

The proper length to diameter proportion may be determined mathematically based on such factors as lubricant viscosity, floss yarn diameter and speed, but the complexity of the model make it much more practical to determine the proper geometry empirically. The die housing will be configured to allow dies of various sizes to be changed easily, and the dies themselves will be designed for low cost fabrication, allowing the selection of an optimal geometry. Because the speed of the moving floss and the rate of lubricant delivery will be carefully controlled, the quantity of lubricant per unit length of product will also be closely controlled.

An alternate means of coating the floss with the lubricant preparation is to pass the moving floss through a bath of the molten lubricant. Upon exiting the bath the floss will pass through a wiping means consisting of a blade, roller, or hole, the purpose of which is to remove excess lubricant. The capacity of the molten lubricant bath will be sized so that the residence time of the lubricant will be held to a minimum to avoid breakdown or denaturation of the therapeutic agent due to prolonged exposure to elevated temperatures.

What is claimed is:

1. A method of fabricating a dental floss comprising the steps of dissolving a predetermined amount of chlorhexidine gluconate in a polyethylene glycol base, where said polyethylene glycol base is comprised of two parts polyethylene glycol of a molecular weight of 3350 and one part of polyethylene glycol of a molecular weight of 1000.

2. The method of claim 1 where said polyethylene glycol base is premelted in combination with chlorhexidine gluconate by means of a premelter, whereby said polyethylene glycol and chlorhexidine combination is placed on said floss by means of a heated grid.

3. The method of claim 2 whereby said heated grid contacts said floss surface thereby dispensing polyethylene and chlorhexidine combination to said floss surface.

4. The method of claim 3 where said dental floss comprises a thread with a coating on said thread, said coating containing chlorhexidine gluconate such that said thread is capable of delivering said coating containing said chlorhexidine gluconate to an affected area at the interproximal surfaces of the teeth in the mouth of a human being, whereby said coating dissolves thereby releasing said chlorhexidine gluconate.

\* \* \* \* \*